United States Patent [19]
Levitt

[11] 4,120,691
[45] Oct. 17, 1978

[54] HERBICIDAL SULFONAMIDES

[75] Inventor: George Levitt, Wilmington, Del.

[73] Assignee: E. I. Du Pont de Nemours and Company, Wilmington, Del.

[21] Appl. No.: 829,823

[22] Filed: Sep. 1, 1977

Related U.S. Application Data

[63] Continuation-in-part of Ser. No. 769,912, Feb. 23, 1977, abandoned, which is a continuation-in-part of Ser. No. 674,668, Apr. 7, 1976, abandoned.

[51] Int. Cl.$^2$ .................... C07D 253/06; A01N 9/16
[52] U.S. Cl. .......................................... 71/93; 71/90; 544/182

[58] Field of Search ...................... 544/182; 71/90, 93

[56] References Cited

FOREIGN PATENT DOCUMENTS 45-9,545  4/1970  Japan.
121,788  2/1967  Netherlands.

*Primary Examiner*—John M. Ford

[57] ABSTRACT

Novel N-(1,2,4-triazin-3-ylaminocarbonyl) arylsulfonamides, such as N-[(5,6-dimethyl-1,2,4-triazin-3-yl)aminocarbonyl]benzene sulfonamide, are useful for regulating the growth of plants.

55 Claims, No Drawings

HERBICIDAL SULFONAMIDES

CROSS-REFERENCE TO RELATED APPLICATIONS

This application is a continuation-in-part of my pending U.S. application Ser. No. 769,912, filed Feb. 23, 1977, now abandoned, which is a continuation-in-part of U.S. application Ser. No. 674,668, filed Apr. 7, 1976, now abandoned.

BACKGROUND

This invention relates to novel N-[(1,2,4-triazin-3-yl)aminocarbonyl]arylsulfonamides.

Netherlands Pat. No. 121,788, published Sept. 15, 1966, discloses the preparation of compounds of Formula (i)

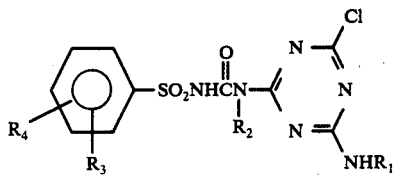

wherein
$R_1$ and $R_2$ may independently be alkyl of 1-4 carbon atoms; and
$R_3$ and $R_4$ may independently be hydrogen, chlorine or alkyl of 1-4 carbon atoms;
and their use as general or selective herbicides.

Compounds of Formula (ii), and their use as antidiabetic agents, are reported in *J. Drug Res.* 6, 123 (1974)

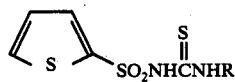

wherein R is pyridyl.

To enable man to carry on manufacturing, transportation, communications and other activity, he must wage a constant battle to prevent encroachment of vegetation into areas in which such activities are performed. Although a wide variety of herbicides is available the need exists for still more effective herbicides that destroy or retard growth of weeds and other vegetation.

SUMMARY OF THE INVENTION

This invention provides compounds of Formula I and their agriculturally suitable salts, suitable agricultural compositions containing them, and methods of using them as general herbicides having both preemergence and postemergence activity, particularly as highly active non-crop industrial herbicides. This invention also relates to methods of using said compounds as plant growth regulants.

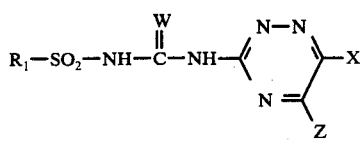

wherein
$R_1$ is

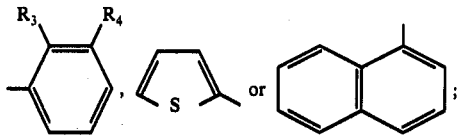

$R_3$ is hydrogen, fluorine, chlorine, bromine, methyl, nitro or methoxy;
$R_4$ is hydrogen, fluorine, chlorine, bromine, methyl or methoxy;
W is oxygen or sulfur;
X and Z are independently hydrogen, methyl, or methoxy; or their agriculturally suitable salts;
provided that X and Z may not be hydrogen simultaneously.

Preferred for their higher activity or favorable cost or both are those compounds of Formula I, defined above, wherein, independently;
(1) W is oxygen; or
(2) $R_1$ is

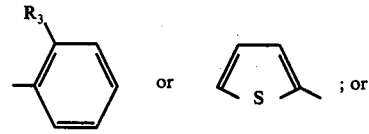

(3) X and Z are independently hydrogen or methyl.

More preferred for their higher activity or more favorable cost or both are those compounds of Formula I wherein
W is oxygen;
$R_1$ is

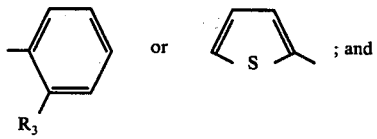

and
X or Z are independently hydrogen or methyl.

Specifically, preferred for their outstanding activity or highly favorable cost or both are:
(1) N-[(5,6-dimethyl-1,2,4-triazin-3-yl)aminocarbonyl]-2-methylbenzenesulfonamide, m.p. 162°–165° C.;
(2) N-[(5,6-dimethyl-1,2,4-triazin-3-yl)aminocarbonyl]-2-chlorobenzenesulfonamide, m.p. 142°–145° C.; and
(3) N-[(5,6-dimethyl-1,2,4-triazin-3-yl)aminocarbonyl]benzenesulfonamide, m.p. 155°–158° C.
(4) N-[(5,6-dimethyl-1,2,4-triazin-3-yl)aminocarbonyl]-2-nitrobenzenesulfonamide, m.p. 105°–110° C.

Synthesis

As shown in Equation 1, the compounds of Formula I can be prepared by combining an appropriate 3-amino-1,2,4-triazine of Formula III with an appropriately substituted sulfonyl isocyanate or isothiocyanate of Formula II; $R_1$, W, X and Z are as previously defined.

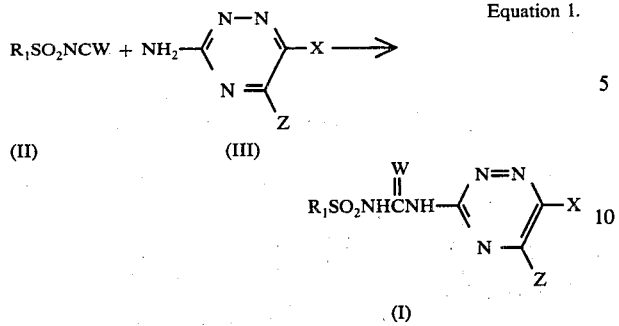

Equation 1.

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate or isothiocyanate to a stirred suspension of the aminotriazine. Since such isocyanates and isothiocyanates usually are liquids, or readily soluble solids, their addition is more easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane, ethyl ether, or pentane, and filtration.

In some cases, it may be possible to obtain an isomeric product from the reaction shown in Equation 1. Such isomeric compounds would result from the addition of compound II to the endocyclic nitrogen atoms of aminotriazine III and have a structure as exemplified below:

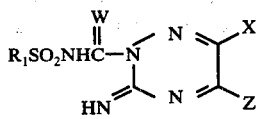

It is to be understood that the addition products resulting from the addition of compound II to the endocyclic nitrogen atoms of triazine III are to be considered a part of this invention.

Intermediate sulfonyl isocyanates of Formula II (wherein W is O) can be prepared by reacting corresponding sulfonamides with phosgene in the presence of n-butyl isocyanate at reflux in a solvent such as chlorobenzene, according to the procedure of H. Ulrich and A. A. Y. Sayigh, *Newer Methods of Preparative Organic Chemistry*, Vol. VI p 223–241, Academic Press, New York and London, W. Foerst. Ed. In cases in which the desired sulfonyl isocyanate cannot be obtained by the above procedure, the sulfonyl urea formed by reaction of butyl isocyanate with the appropriate sulfonamide is treated with phosgene according to the above reference.

The preparation of sulfonamides from ammonium hydroxide and sulfonyl chlorides is widely reported in the literature, e.g. Crossley et al., *J. Am. Chem. Soc.* 60, 2223 (1938).

Certain sulfonyl chlorides are best prepared by chlorosulfonation of a substituted benzene, naphthalene, or thiophene in carbon tetrachloride according to the teaching of H. T. Clarke et al. *Org. Synth.* Coll. Vol. 1, 2nd Ed. 1941, p 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.* 25 1824 (1960).

Sulfonyl isothiocyanates can be prepared by treatment of sulfonamides with carbon disulfide and potassium hydroxide followed by reaction of the dipotassium salt with phosgene according to the teaching of K. Hartke, *Arch. Pharm.*, 299, 174 (1966).

The synthesis of 3-amino-1,2,4-triazines has been reviewed in "The Chemistry of Heterocyclic Compounds", Volume X, a series edited by A. Weissberger and published by Interscience Publishers, Inc., New York and London in 1956.

Agriculturally suitable salts of compounds of Formula I are also useful herbicides and can be prepared by a number of ways known to the art. For example, metal salts can be made by treating compounds of Formula I with a solution of an alkali or alkaline earth metal salt having a sufficiently basic anion (e.g. hydroxide, alkoxide, carbonate or hydride). Quaternary ammonium salts can be made by similar techniques.

Salts of compounds of Formula I can also be prepared by exchange of one cation for another. Cationic exchange can be effected by direct treatment of an aqueous solution of a salt of a compound of Formula I (e.g. alkali metal or quaternary ammonium salt) with a solution containing the cation to be exchanged. This method is most effective when the desired salt containing the exchanged cation is insoluble in water and can be separated by filtration.

Exchange may also be effected by passing on aqueous solution of a salt of a compound of Formula I (e.g. an alkali metal or quaternary ammonium salt) through a column packed with a cation exchange resin containing the cation to be exchanged. In this method, the cation of the resin is exchanged for that of the original salt and the desired product is eluted from the column. This method is particularly useful when the desired salt is water-soluble.

Acid addition salts, useful in this invention, can be obtained by reacting a compound of Formula I with a suitable acid, e.g. p-toluenesulfonic acid, trichloroacetic acid or the like.

The preparation of compounds of this invention is further illustrated by the following specific examples wherein temperatures are in degrees C.

EXAMPLE 1

N-[(5,6-Dimethyl-1,2,4-triazin-3-yl)aminocarbonyl]benzenesulfonamide

To a dry, well stirred mixture of 6 g of 3-amino-5,6-dimethyl-1,2,4-triazine in 100 ml of methylene chloride at ambient temperature and pressure was added 9 g of benzenesulfonyl isocyanate. The mixture was stirred for 4 hours and the precipitated product removed by filtration. After washing with 1-chlorobutane, the product melted at 155°–158°.

EXAMPLE 2

N-[(5,6-dimethyl-1,2,4-triazin-3-yl)aminocarbonyl]-2-chlorobenzenesulfonamide

To a dry, well stirred mixture of 12 g of 3-amino-5,6-dimethyl-1,2,4-triazine in 100 ml of acetonitrile at ambient temperature and pressure was added 21 g of 2- chlorobenzenesulfonyl isocyanate. The mixture was stirred for 6 hours and the precipitated product removed by filtration. After washing with diethyl ether, the product melted at 142°–145°.

By using the procedure of Example 1 or 2 with an equivalent amount of the appropriate aminotriazine and the appropriately substituted benzenesulfonyl isocyanate, the compounds of Tables I–III can be prepared:

TABLE I

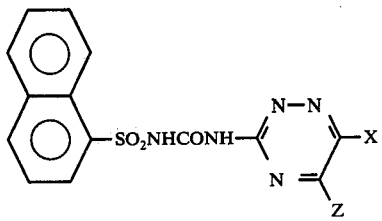

| R₃ | R₄ | W | X | Z | m.p. |
|---|---|---|---|---|---|
| H | H | S | CH₃ | CH₃ | 188 – 190 |
| Br | H | O | CH₃ | CH₃ | |
| NO₂ | H | O | CH₃ | CH₃ | 105 – 110 |
| Cl | H | S | CH₃ | CH₃ | |
| F | H | O | CH₃ | CH₃ | 163 – 165 |
| OCH₃ | H | O | CH₃ | CH₃ | |
| CH₃ | H | O | CH₃ | CH₃ | 162 – 165 |
| CH₃ | H | S | CH₃ | CH₃ | 142 – 144 |
| H | Br | O | CH₃ | CH₃ | |
| H | Cl | O | CH₃ | CH₃ | 198 – 199 |
| H | F | O | CH₃ | CH₃ | |
| H | OCH₃ | O | CH₃ | CH₃ | |
| H | CH₃ | O | CH₃ | CH₃ | |
| Cl | Cl | O | CH₃ | CH₃ | 168 – 171 |
| Cl | OCH₃ | O | CH₃ | CH₃ | |
| Cl | CH₃ | O | CH₃ | CH₃ | |
| F | Cl | O | CH₃ | CH₃ | 157 – 161 |
| OCH₃ | Cl | O | CH₃ | CH₃ | |
| CH₃ | Cl | O | CH₃ | CH₃ | 157 – 159 |
| CH₃ | CH₃ | O | CH₃ | CH₃ | |
| H | H | O | OCH₃ | OCH₃ | |
| Br | H | O | OCH₃ | OCH₃ | |
| Cl | H | O | OCH₃ | OCH₃ | |
| F | H | O | OCH₃ | OCH₃ | |
| OCH₃ | H | O | OCH₃ | OCH₃ | |
| CH₃ | H | O | OCH₃ | OCH₃ | |
| H | Br | O | OCH₃ | OCH₃ | |
| H | Cl | O | OCH₃ | OCH₃ | |
| H | F | O | OCH₃ | OCH₃ | |
| H | CH₃ | O | OCH₃ | OCH₃ | |
| Cl | Cl | O | OCH₃ | OCH₃ | |
| Cl | OCH₃ | O | OCH₃ | OCH₃ | |
| Cl | CH₃ | O | OCH₃ | OCH₃ | |
| F | Cl | O | OCH₃ | OCH₃ | |
| CH₃ | Cl | O | OCH₃ | OCH₃ | |
| CH₃ | CH₃ | O | OCH₃ | OCH₃ | |
| H | H | O | CH₃ | OCH₃ | |
| H | H | S | CH₃ | OCH₃ | |
| Br | H | O | CH₃ | OCH₃ | |
| Cl | H | O | CH₃ | OCH₃ | |
| F | H | O | CH₃ | OCH₃ | |
| OCH₃ | H | O | CH₃ | OCH₃ | |
| CH₃ | H | O | CH₃ | H | |
| H | Br | O | CH₃ | OCH₃ | |
| H | Cl | O | CH₃ | OCH₃ | |
| H | F | O | CH₃ | OCH₃ | |
| H | OCH₃ | O | CH₃ | OCH₃ | |
| H | CH₃ | O | CH₃ | OCH₃ | |
| Cl | Cl | O | CH₃ | OCH₃ | |
| Cl | OCH₃ | O | CH₃ | OCH₃ | |
| Cl | CH₃ | O | CH₃ | OCH₃ | |
| F | Cl | O | CH₃ | OCH₃ | |
| CH₃ | Cl | O | CH₃ | OCH₃ | |
| CH₃ | CH₃ | O | CH₃ | OCH₃ | |
| H | H | O | H | OCH₃ | |
| Br | H | O | H | OCH₃ | |
| Cl | H | O | H | OCH₃ | |
| F | H | O | H | OCH₃ | |
| OCH₃ | H | O | H | OCH₃ | |
| CH₃ | H | O | H | OCH₃ | |
| H | Br | O | H | OCH₃ | |
| H | Cl | O | H | OCH₃ | |
| H | F | O | H | OCH₃ | |
| H | OCH₃ | O | H | OCH₃ | |
| H | CH₃ | O | H | OCH₃ | |
| Cl | Cl | O | H | OCH₃ | |
| Cl | OCH₃ | O | H | OCH₃ | |
| Cl | CH₃ | O | H | OCH₃ | |
| F | Cl | O | H | OCH₃ | |
| OCH₃ | Cl | O | H | OCH₃ | |
| CH₃ | CH₃ | O | H | OCH₃ | |

TABLE II naphthyl–SO₂NHCONH–[triazine]–X, Z

| X | Z | m.p. |
|---|---|---|
| CH₃ | CH₃ | 126 – 131 |
| CH₃ | H | |
| H | CH₃ | |

TABLE III thienyl–SO₂NHCONH–[triazine]–X, Z

| X | Z | m.p. |
|---|---|---|
| CH₃ | CH₃ | 144 – 146 |
| CH₃ | H | |
| H | CH₃ | |

Sulfonyl isocyanates II react with a mixture of 3-amino-5-methyl-1,2,4-triazine and 3-amino-6-methyl-1,2,4-triazine to give mixed products of Table IV which exhibit herbicidal properties described for this invention.

TABLE IV

| R₃ | R₄ | W | X | Z | | m.p. |
|---|---|---|---|---|---|---|
| CH₃ | H | O | H | CH₃ | 90% | 161 – 164 |
| | | | CH₃ | H | 10% | |
| CH₃ | H | O | H | CH₃ | 20% | 150 – 153 |
| | | | CH₃ | H | 80% | |
| Cl | H | O | H | CH₃ | 50% | 145 – 152 |
| | | | CH₃ | H | 50% | |
| F | Cl | O | H | CH₃ | 50% | 134 – 140 |
| | | | CH₃ | H | 50% | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1 to 99% by weight of active ingredient(s) and at least one of a) about 0.1 to 20% surfactant(s) and b) about 1 to 99.9% solid or liquid diluent(s). More specifically, they will contain these ingredients in the following approximate proportions:

TABLE V

| | Active Ingredient | Diluent(s) | Surfactant(s) |
|---|---|---|---|
| Wettable Powders | 20 – 90 | 0 – 74 | 1 – 10 |
| Oil Suspensions, Emulsions, Solutions (including Emulsifiable Concentrates) | 3 – 50 | 40 – 95 | 0 – 15 |
| Aqueous Suspensions | 10 – 50 | 40 – 84 | 1 – 20 |
| Dusts | 1 – 25 | 70 – 99 | 0 – 5 |
| Granules and Pellets | 0.1 – 95 | 5 – 99.9 | 0 – 15 |
| High Strength Compositions | 90 – 99 | 0 – 10 | 0 – 2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, New York, 1963, pp. 8–59 ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 3

| Wettable Powder | |
|---|---|
| N-[(5,6-dimethyl-1,2,4-triazin-3-yl)-aminocarbonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended.

EXAMPLE 4

| Extruded Pellet | |
|---|---|
| N-[(5,6-dimethyl-1,2,4-triazin-3-yl)-aminocarbonyl]-2-chloro-benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 5

| Oil Suspension | |
|---|---|
| N-[(5,6-dimethyl-1,2,4-triazin-3-yl)-aminocarbonyl]benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE 6

| Wettable Powder | |
|---|---|
| N-[(5,6-dimethyl-1,2,4-triazin-3-yl)-aminocarbonyl]-2-chloro-benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 7

| Wettable Powder: | |
|---|---|
| N-[(5,6-dimethyl-1,2,4-triazin-3-yl)- | 95% |

-continued

| Wettable Powder: | |
|---|---|
| aminocarbonyl]-2-chlorobenzene-sulfonamide | |
| dioctyl sodium sulfosuccinate | 0.1% |
| synthetic fine silica | 4.9% |

The ingredients are blended and ground in a hammer-mill to produce particles essentially all below 100 microns. The material is sifted through a U.S.S. No. 50 screen and then packaged.

EXAMPLE 8

| Wettable Powder: | |
|---|---|
| N-[(5,6-dimethyl-1,2,4-triazin-3-yl)-aminocarbonyl]-2-chlorobenzene-sulfonamide | 40% |
| sodium ligninsulfonate | 20% |
| montmorillonite clay | 40% |

The ingredients are thoroughly bended, coarsely hammer-milled and then air-milled to produce particles essentially all below 10 microns in size. The material is reblended and then packaged.

EXAMPLE 9

| Low Strength Granule | |
|---|---|
| N-[(5,6-dimethyl-1,2,4-triazin-3-yl)-aminocarbonyl]-2-chlorobenzene-sulfonamide | 1% |
| N,N-dimethylformamide | 9% |
| attapulgite granules (U.S.S. 20 – 40 mesh). | 90% |

The active ingredient is dissolved in the solvent and the solution is sprayed upon dedusted granules in a rotating blender. After spraying of the solution has been completed, the blender is allowed to run for a short period and then the granules are packaged.

EXAMPLE 10

| Aqueous Suspension | |
|---|---|
| N-[(5,6-dimethyl-1,2,4-triazin-3-yl)-aminocarbonyl]-2-methylbenzene-sulfonamide | 40% |
| Polyacrylic acid thickener | 0.3% |
| Dodecylphenol polyethylene glycol ether | 0.5% |
| Disodium phosphate | 1% |
| Monosodium phosphate | 0.5% |
| Polyvinyl alcohol | 1.0% |
| Water | 56.7% |

The ingredients are blended and ground together in a sand mill to produce particles essentially all under 5 microns in size.

EXAMPLE 11

| Solution | |
|---|---|
| N-[(5,6-dimethyl-1,2,4-triazin-3-yl)-aminocarbonyl]benzenesulfonamide, sodium salt | 5% |
| water | 95% |

The salt is added directly to the water with stirring to produce the solution, which may then be packaged for use.

EXAMPLE 12

| Low Strength Granule | |
|---|---|
| N-[(5,6-dimethyl-1,2,4-triazin-3-yl)-aminocarbonyl]-2-chlorobenzene-sulfonamide | 0.1% |
| attapulgite granules (U.S.S. 20 – 40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 13

| Wettable Powder | |
|---|---|
| N-[(5,6-dimethyl-1,2,4-triazin-3-yl)-aminocarbonyl]-2-methylbenzene-sulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles of active essentially all below 10 microns in diameter. The product is reblended before packaging.

EXAMPLE 14

| Granule | |
|---|---|
| wettable powder of Example 13 | 5% |
| attapulgite granules (U.S.S. 20 – 40 mesh; 0.84 – 0.42 mm) | 95% |

A slurry of wettable powder containing ≈25% solids is sprayed on the surface of attapulgite granules in a double-cone blender. The granules are dried and packaged.

EXAMPLE 15

| Oil Suspension | |
|---|---|
| N-[(5,6-dimethyl-1,2,4-triazin-3-yl)-aminocarbonyl]-2-chloro-benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting suspension may be applied directly, but preferably after being extended with oils or emulsified in water.

EXAMPLE 16

| High Strength Concentrate | |
|---|---|
| N-[(5,6-dimethyl-1,2,4-triazin-3-yl)-aminocarbonyl]benzenesulfonamide | 99% |
| silica aerogel | 0.5% |
| synthetic amorphous silica | 0.5 |

The ingredients are blended and ground in a hammer mill to produce a material essentially all passing a U.S.S.

No. 50 sieve (0.3 mm opening). The concentrate may be formulated further if necessary.

EXAMPLE 17

| Granule | |
| --- | --- |
| N-[(5,6-dimethyl-1,2,4-triazin-3-yl)-aminocarbonyl]-benzenesulfonamide | 80% |
| wetting agent | 1% |
| crude ligninsulfonate salt (containing 5 – 20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

The compounds of Formula I can be formulated using the procedures of Examples 3–17.

UTILITY

The compounds of Formula I are useful as herbicides. They may be applied either pre- or postemergence for the control of undesired vegetation. By properly selecting rate and time of application, compounds of this invention may be used to modify plant growth beneficially.

The precise amount of the compound of Formula I to be used in any given situation will vary according to the particular end result desired, the use involved, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.1 to 20 kg/ha with a preferred range of 0.2 to 10 kg/ha. The lower rates of the range will generally by selected for lighter soils, for plant growth modification, weed control in crops or in situations in which maximum persistence is not necessary.

The compounds of Formula I may be combined with other herbicides and are particularly useful in combination with 3-(3,4-dichlorophenyl)-1,1-dimethylurea, the triazines such as 2,4-bis(isopropylamino)-6-(methylthio)-s-triazine, the uracils such as 5-bromo-3-sec-butyl-6-methyluracil, N-(phosponomethyl)glycine, 3-cyclohexyl-1-methyl-6-dimethylamino-s-triazine-2,4(1H,3H)-dione, N,N-dimethyl-2,2-diphenylacetamide, 2,4-dichlorophenoxyacetic acid (and closely related compounds), 4-amino-6-tert-butyl-3-(methylthio)1,2,4-triazin-5(4H)-one (Lexone®), 3-(3,4-dichlorophenyl)-1-methoxy-1-methylurea (Lorox®), 1,1'-dimethyl-4,4'-bipyridinium ion and monosodium methanearsonate.

The activity of these compounds was discovered in greenhouse tests. The tests are described and the data resulting from them are shown below.

TEST PROCEDURE A

Seeds of crabgrass (*Digitaria* sp.), barnyardgrass (*Echinochloa crusgalli*), wild oats (*Avena fatua*), *Cassia tora*, morningglory (*Ipomoea* sp.), cocklebur (*Xanthium* sp.), sorghum, corn, soybean, rice, wheat and nut-sedge tubers were planted in a growth medium and treated preemergence with the chemicals dissolved in a non-phytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three–five leaves were sprayed. Treated plants and controls were maintained in a greenhouse for 16 days, then all species were compared to controls and visually rated for response to treatment.

Ratings for compounds tested by this procedure are recorded in Table VI.

0 = no effect
& or 10 = maximum effect
B = burn
C = chlorosis or necrosis
E = emergence inhibition
G = growth retardation
H = formative effects
P = terminal bud kill
S = albinism
U = unusual pigmentation
6Y = abscised buds or flowers
X = axillary stimulation
6F = delayed flowering It will be seen that the compounds of Formula I possess excellent herbicidal properties.

TABLE VI

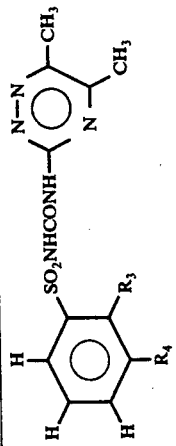

| $R_3$ | $R_4$ | Mode of Application | Rate Kg/Ha | Bush Bean | Cotton | Sorghum | Corn | Soybean | Wheat | Wild Oats | Rice | Barnyardgrass | Crabgrass | Morningglory | Cocklebur | Cassia | Nutsedge |
|---|---|---|---|---|---|---|---|---|---|---|---|---|---|---|---|---|---|
| H | H | Post | 2.0 | 2H 8G 6Y | 2C 3H 5X | 9H | 1H 5G | 2H 7G 7X 6H | 4H | 0 | 7H 5X | 6H | 0 | 5C | 8H &P | 1H | 0 |
|   |   | Post | 2.0 |   |   |   |   |   |   |   |   |   |   |   |   |   |   |
|   |   | Pre | 2.0 | 1H 8G 6Y | 2H 3G | 9G | 2C 8G | 2H 9G | 7G | 7G | &E | 9H | 1H | 6G | 7G | 7G | 6G |
| CH₃ | H | Post | 2.0 |   |   | 2C 8G | 2C 3H 8G 9G | 2H 9G 4H | 1C 6G | 2G | 2C 8G | 1C 9H | 1C 6G | 3C 9G | 2C 8G | 1C 7G | 1C 8G |
|   |   | Pre | 2.0 |   |   | &E | 4H 9G 9G | 4H 9G 1C 8H | 9H | 2C 8G 0 | &E | 2C 9H 6H | 4G | 8G | | 8G | &E |
| F | H | Post | 0.4 | 2S 7G 6Y | 1C | 1C 5H | 1C 2H | 1C 8H | 2G | &E | 1C | 2C 6H | 1C | 5G | &P 7G | 3C | 1C |
|   |   | Pre | 0.4 |   |   | 1C 8G 1H 7G | 1C 8G 2C 9H | 9G 2G 3C 9G | 2G 5G | &E 0 | 2C 1C 8G | 1C 8G 1C 7H | 1C 5G 5G | 8G 1B 7G | 7C 1C 8G | 1C 2C 3G | 7G 1C 5G |
| Cl | H | Post | 0.4 | 2S 7G 6Y | 4G | 9G | 1C 9G 0 | 9H 1C 4G | 1C 9G 0 | 1C 3G 0 | &E 0 | 1H 8G 0 | 5G 2G | 9G 1C | 8H 6F | 8G 0 | 9G 0 |
|   |   | Pre | 0.4 |   |   |   |   |   |   |   |   |   |   |   |   |   |   |
| H | Cl | Post | 0.4 | 1C 6F 6Y | 0 | 0 | 0 | 1H | 0 | 0 | 8H | 0 | 0 | 0 | 0 | 0 | 0 |
|   |   | Pre | 0.4 |   |   | 0 | 0 | 0 | 0 | 0 | 0 | 0 | 0 | 0 | 6F | 0 | 0 |
| F | Cl | Post | 2.0 | 5S 7G 6Y | 1C | 1C 6G 9G | 1C 4G 7H 9G | 1H 8H 9H | 3G 0 | 0 0 | 8H 9G | 1C 1C 6H | 0 2G | 3G 2B | 1C 5H | 1C | 3G |
|   |   | Pre | 2.0 |   |   |   |   |   |   |   |   |   |   |   |   |   |   |
| Cl | Cl | Post | 2.0 | 3H 9G 6Y | 1B | 9H | 9G | 9H | 9G | 0 | &E 8G | 2H 8G 0 | 1C | 8G | &E | 8G | 2G |
|   |   | Pre | 2.0 |   |   | 8G | 4G | 4G | 0 | 2G | 8G | 1C | 0 | 1C 5G | 3G | 2G | 2G |
| CH₃ | Cl | Post | 2.0 | 1H | 2G | 8H | 6G | 2G | 5G | 0 | &E | 2G | 0 | 9G | 9G | 5G | 0 |
|   |   | Pre | 2.0 |   |   |   |   |   |   |   |   |   |   |   |   |   |   |

TABLE VI-continued

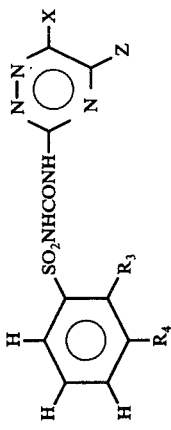

| R₃ | R₄ | X | Z | Rate Kg/Ha | Mode of Application | Bush Bean | Cotton | Sorghum | Corn | Soybean | Wheat | Wild Oats | Rice | Barnyardgrass | Crabgrass | Morningglory | Cocklebur | Cassia | Nutsedge |
|---|---|---|---|---|---|---|---|---|---|---|---|---|---|---|---|---|---|---|---|
| CH₃ | H | 90%H 10%CH₃ | CH₃ H | 2.0 2.0 | Post Post | 3C 9G | 3C 5H 7G | 3U 9G | 9C 9G | 1C 2H 9G | 8G 9H | 9H 9H | 5C 9G | 2C 9H | 3C 8G | 5C 9G | 5C 9G | 1C 5G | 5C 9G |
| | | | | 2.0 2.0 | Post Pre | | | 2C 9G 1C 3H 9G | 9G 2H 8G | 1C 8G | 9H 0 | 9H 1C 7G | &E 4C 9G | 1C 9H 1C 6G | 1C 9G 0 | 9G 1C 7G | 9G 1C 8G | 7G 3C | &E 1C 9G |
| CH₃ | H | 80%CH₃ 20%H | H CH₃ | 2.0 | Post | 3H 5G 6Y | 2G | | 2H 8G | | | | | | | | | | |
| | | | | 2.0 | Pre | | | | | | | | | | | | | | |
| Cl | H | 50%CH₃ 50%H | H CH₃ | 2.0 2.0 | Post Post | 2H 8G 6Y | 1H | 9H | 6H 9G | 3H 9G | 8G 0 | 8G 0 | &E 6G | 9H 1B 8H | 0 0 | 9G 3H 8G | 1H 9G 2H | 2C 9G 2H | &E 0 |
| | | | | 2.0 2.0 | Pre Pre | | | | | | | | | | | | | | |
| F | Cl | 50%CH₃ 50%H | H CH₃ | 2.0 2.0 | Post Post | 3H 7G | 1H | 9G | 9G 0 | 5H 0 | 6G 0 | 3G 0 | &E 0 | 8H 0 | 0 0 | 9G 0 | 9G 0 | 2C 0 | &E 0 |
| | | | | 2.0 2.0 | Pre Pre | | | | | | | | | | | | | | |
| NO₂ | H | CH₃ | CH₃ | 2.0 2.0 | Post Post | 3H 6F | 5G 3C | 7H 0 | 7H 5G 3H | 2H 10G 5H | 0 0 | 0 0 | 9H 5G | 0 0 | 0 5G | 5G 10C | 7G 0 | 5G 9C | 0 10G 8C |
| | | | | 0.4 0.4 | Pre Post | 3H | | 4G | 5G 3C | 8G | 3G | 3G 3H | 9G | 7G 5H | 3G | 6G | 3G 5H | 8G 5C | 10E |

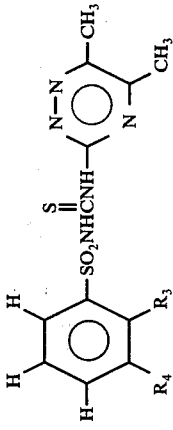

| R₃ | R₄ | Rate Kg/Ha | Mode of Application | Bush Bean | Corn | Soybean | Wheat | Wild Oats | Rice | Barnyardgrass | Crabgrass | Morningglory | Cocklebur | Cassia | Nutsedge |
|---|---|---|---|---|---|---|---|---|---|---|---|---|---|---|---|
| H | H | 2.0 2.0 | Post Pre | 0 0 | 0 0 | 0 2H 0 | 0 0 | 0 0 | 5G 0 | 0 0 | 2G 0 | 0 0 | 0 0 | 0 2G 1C | 5G 0 |
| CH₃ | H | 2.0 2.0 | Post Pre | 6G 0 | 0 0 | | 0 0 | 0 0 | 0 0 | 0 0 | 3H 0 | 0 4G | 0 0 |

TABLE VI-continued

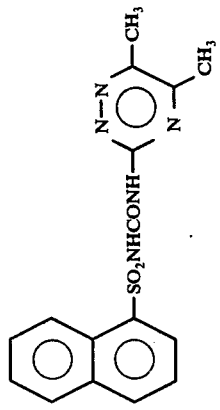

| Mode of Appli-cation | Rate Kg/Ha | Bush Bean | Cotton | Sor-ghum | Corn | Soybean | Wheat | Wild Oats | Rice | Barnyardgrass | Crabgrass | Morningglory | Cocklebur | Cassia | Nutsedge |
|---|---|---|---|---|---|---|---|---|---|---|---|---|---|---|---|
| Post | 2.0 | 1C 8G 6Y | 0 | 1C 5G | 0 | 0 | 0 | 0 | 7G | 0 | 0 | 7G | 1C | 1C | 0 |
| Post | 2.0 | | | | | | | | | | | | | | |
| Post | 2.0 | | | | | | | | | | | | | | |
| Pre | 2.0 | | | 2C 7G | 5G | 0 | 0 | 0 | &E | 0 | 2G | 7G | 9G | 7G | 0 |
| Pre | 2.0 | | | | | | | | | | | | | | |

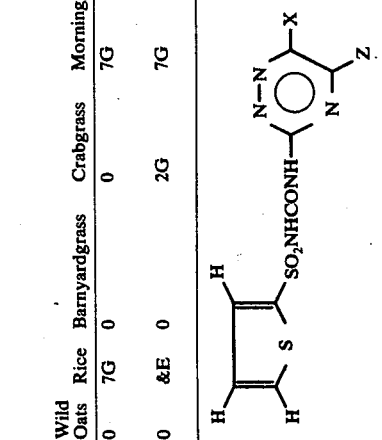

| X | Z | Mode of Appli-cation | Rate Kg/Ha | Bush Bean | Cotton | Sor-ghum | Corn | Soybean | Wheat | Wild Oats | Rice | Barnyardgrass | Crabgrass | Morningglory | Cocklebur | Cassia | Nutsedge |
|---|---|---|---|---|---|---|---|---|---|---|---|---|---|---|---|---|---|
| CH₃ | CH₃ | Post | 2.0 | 3C 8G 6Y | 2C 2H 6G | 9G | 2H 7G | 2C 7G | 2H | 0 | 2C 9G | 9H | 1C 5G | 6G | 7G | 8G | 2C | 2G |
| | | Post | 2.0 | | | | | | | | | | | | | | |
| | | Post | 2.0 | | | 2U 9G | 1C 9G | 9H | 8C | 1C 5G | &E | 2C 9H | 5G | 8G | 8G | 6G | 6G |
| | | Pre | 2.0 | | | | | | | | | | | | | | |
| | | Pre | 2.0 | | | | | | | | | | | | | | |

In addition to being broad-spectrum herbicides for non-selective weed control applications, the present compounds may be used to modify the growth of selected plant species. Test B, described below, illustrates the beneficial effect of one of the compounds of the invention on the soluble solids content of sweet sorghum.

TEST B

Tracy sweet sorghum plants grown one per 15 cm pot to a stage just prior to head emergence were sprayed with the compound given below. Visual effects were noted about 3 weeks after spraying; then at 4 weeks plants were harvested and soluble solids determined at the centers of the top, middle, and bottom thirds of each stalk. Percent soluble solids was increased and growth and flowering were restricted. See Table VII for results.

TABLE VII

| Compound | Kg/Ha | 3-Week Response Rating [1] | Percent Soluble Solids in Various Sections of Sorghum Stalks | | |
|---|---|---|---|---|---|
| | | | Bottom | Middle | Top |
| (structure shown) | 0.125 | 8G,F,3X | 12.3 | 12.0 | 10.5 |
| | 0.5 | 9G,F,1C,3X | 13.5 | 12.5 | 12.9 |
| | 2.0 | 9G,F,1C,3X | 13.1 | 12.3 | 10.1 |
| Solvent Control | — | 0 | 10.9 | 12.6 | 11.0 |

[1] F = flowering delayed.

What is claimed is:

1. A compound having the formula:

$$R_1-SO_2-NH-\overset{W}{\underset{\parallel}{C}}-NH-\underset{N=}{\overset{N-N}{\diagdown}}\diagup^X_Z$$

wherein
$R_1$ is

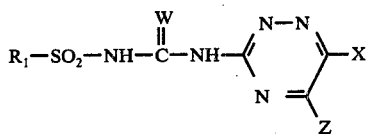

$R_3$ is hydrogen, fluorine, chlorine, bromine, nitro, methyl or methoxy;
$R_4$ is hydrogen, fluorine, chlorine, bromine, methyl or methoxy;
W is oxygen or sulfur;
X and Z are independently hydrogen, methyl or methoxy; or an agriculturally suitable salt thereof;
provided that X and Z may not be hydrogen simultaneously.

2. A compound of claim 1 wherein W is oxygen.
3. A compound of claim 1 wherein $R_1$ is

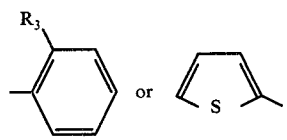

4. A compound of claim 3 wherein W is oxygen.
5. A compound of claim 1 wherein X and Z are independently hydrogen or methyl.
6. A compound of claim 5 wherein W is oxygen.
7. A compound of claim 6 wherein $R_1$ is

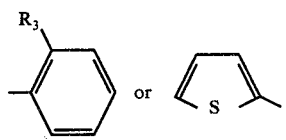

8. A compound of claim 1 which is N-[(5,6-dimethyl-1,2,4-triazin-3-yl)aminocarbonyl]2-methylbenzenesulfonamide.
9. A compound of claim 1 which is N-[(5,6-dimethyl-1,2,4-triazin-3-yl)aminocarbonyl]-2-chlorobenzenesulfonamide.
10. A compound of claim 1 which is N-[(5,6-dimethyl-1,2,4-triazin-3-yl)aminocarbonyl]benzenesulfonamide.
11. A compound of claim 1 which is N-[(5,6-dimethyl-1,2,4-triazin-3-yl)aminocarbonyl]-2-nitrobenzenesulfonamide.
12. A composition suitable for controlling the growth of undesired vegetation which comprises an effective amount of a compound of claim 1 and at least one of the following: surfactant, solid or liquid diluent.
13. A composition suitable for controlling the growth of undesired vegetation which comprises an effective amount of a compound of claim 2 and at least one of the following: surfactant, solid or liquid diluent.
14. A composition suitable for controlling the growth of undesired vegetation which comprises an effective amount of a compound of claim 3 and at least one of the following: surfactant, solid or liquid diluent.
15. A composition suitable for controlling the growth of undesired vegetation which comprises an effective amount of a compound of claim 4 and at least one of the following: surfactant, solid or liquid diluent.
16. A composition suitable for controlling the growth of undesired vegetation which comprises an effective amount of a compound of claim 5 and at least one of the following: surfactant, solid or liquid diluent.

17. A composition suitable for controlling the growth of undesired vegetation which comprises an effective amount of a compound of claim 6 and at least one of the following: surfactant, solid or liquid diluent.

18. A composition suitable for controlling the growth of undesired vegetation which comprises an effective amount of a compound of claim 7 and at least one of the following: surfactant, solid or liquid diluent.

19. A composition suitable for controlling the growth of undesired vegetation which comprises an effective amount of the compound of claim 8 and at least one of the following: surfactant, solid or liquid diluent.

20. A composition suitable for controlling the growth of undesired vegetation which comprises an effective amount of the compound of claim 9 and at least one of the following: surfactant, solid or liquid diluent.

21. A composition suitable for controlling the growth of undesired vegetation which comprises an effective amount of the compound of claim 10 and at least one of the following: surfactant, solid or liquid diluent.

22. A composition suitable for controlling the growth of undesired vegetation which comprises an effective amount of the compound of claim 11 and at least one of the following: surfactant, solid or liquid diluent.

23. A method for controlling the growth of undesired vegetation which comprises applying to the locus of the undesired vegetation an effective amount of a compound of claim 1.

24. A method for controlling the growth of undesired vegetation which comprises applying to the locus of the undesired vegetation an effective amount of a compound of claim 2.

25. A method for controlling the growth of undesired vegetation which comprises applying to the locus of the undesired vegetation an effective amount of a compound of claim 3.

26. A method for controlling the growth of undesired vegetation which comprises applying to the locus of the undesired vegetation an effective amount of a compound of claim 4.

27. A method for controlling the growth of undesired vegetation which comprises applying to the locus of the undesired vegetation an effective amount of a compound of claim 5.

28. A method for controlling the growth of undesired vegetation which comprises applying to the locus of the undesired vegetation an effective amount of a compound of claim 6.

29. A method for controlling the growth of undesired vegetation which comprises applying to the locus of the undesired vegetation an effective amount of a compound of claim 7.

30. A method for controlling the growth of undesired vegetation which comprises applying to the locus of the undesired vegetation an effective amount of the compound of claim 8.

31. A method for controlling the growth of undesired vegetation which comprises applying to the locus of the undesired vegetation an effective amount of the compound of claim 9.

32. A method for controlling the growth of undesired vegetation which comprises applying to the locus of the undesired vegetation an effective amount of the compound of claim 10.

33. A method for controlling the growth of undesired vegetation which comprises applying to the locus of the undesired vegetation an effective amount of the compound of claim 11.

34. A method for regulating the growth of vegetation which comprises applying to the locus of the vegetation an effective amount of a compound of claim 1.

35. A method for regulating the growth of vegetation which comprises applying to the locus of the vegetation an effective amount of a compound of claim 2.

36. A method for regulating the growth of vegetation which comprises applying to the locus of the vegetation an effective amount of a compound of claim 3.

37. A method for regulating the growth of vegetation which comprises applying to the locus of the vegetation an effective amount of a compound of claim 4.

38. A method for regulating the growth of vegetation which comprises applying to the locus of the vegetation an effective amount of a compound of claim 5.

39. A method for regulating the growth of vegetation which comprises applying to the locus of the vegetation an effective amount of a compound of claim 6.

40. A method for regulating the growth of vegetation which comprises applying to the locus of the vegetation an effective amount of a compound of claim 7.

41. A method for regulating the growth of vegetation which comprises applying to the locus of the vegetation an effective amount of the compound of claim 8.

42. A method for regulating the growth of vegetation which comprises applying to the locus of the vegetation an effective amount of the compound of claim 9.

43. A method for regulating the growth of vegetation which comprises applying to the locus of the vegetation an effective amount of the compound of claim 10.

44. A method for regulating the growth of vegetation which comprises applying to the locus of the vegetation an effective amount of the compound of claim 11.

45. A composition suitable for use as a growth regulant which comprises an effective amount of a compound of claim 1 and at least one of the following: surfactant, solid or liquid diluent.

46. A composition suitable for use as a growth regulant which comprises an effective amount of a compound of claim 2 and at least one of the following: surfactant, solid or liquid diluent.

47. A composition suitable for use as a growth regulant which comprises an effective amount of a compound of claim 3 and at least one of the following: surfactant, solid or liquid diluent.

48. A composition suitable for use as a growth regulant which comprises an effective amount of a compound of claim 4 and at least one of the following: surfactant, solid or liquid diluent.

49. A composition suitable for use as a growth regulant which comprises an effective amount of a compound of claim 5 and at least one of the following: surfactant, solid or liquid diluent.

50. A composition suitable for use as a growth regulant which comprises an effective amount of a compound of claim 6 and at least one of the following: surfactant, solid or liquid diluent.

51. A composition suitable for use as a growth regulant which comprises an effective amount of a compound of claim 7 and at least one of the following: surfactant, solid or liquid diluent.

52. A composition suitable for use as a growth regulant which comprises an effective amount of the compound of claim 8 and at least one of the following: surfactant, solid or liquid diluent.

53. A composition suitable for use as a growth regulant which comprises an effective amount of the compound of claim 9 and at least one of the following: surfactant, solid or liquid diluent.

54. A composition suitable for use as a growth regulant which comprises an effective amount of the compound of claim 10 and at least one of the following: surfactant, solid or liquid diluent.

55. A composition suitable for use as a growth regulant which comprises an effective amount of the compound of claim 11 and at least one of the following: surfactant, solid or liquid diluent.

* * * * *